(12) United States Patent
Saari-Nordhaus et al.

(10) Patent No.: US 8,681,330 B2
(45) Date of Patent: Mar. 25, 2014

(54) EVAPORATIVE LIGHT SCATTERING DETECTOR

(75) Inventors: Raaidah B. Saari-Nordhaus, Antioch, IL (US); Washington J. Mendoza, Lake in the Hills, IL (US); Michael F. Wicnienski, Lake Villa, IL (US); Alexandra M. Kuch, Evanston, IL (US); James M. Anderson, Arlington Heights, IL (US)

(73) Assignee: Alltech Associates, Inc., Columbia, MD (US)

( * ) Notice: Subject to any disclaimer, the term of this patent is extended or adjusted under 35 U.S.C. 154(b) by 858 days.

(21) Appl. No.: 12/224,929

(22) PCT Filed: Feb. 27, 2007

(86) PCT No.: PCT/US2007/004989
§ 371 (c)(1),
(2), (4) Date: May 26, 2010

(87) PCT Pub. No.: WO2007/103044
PCT Pub. Date: Sep. 13, 2007

(65) Prior Publication Data
US 2011/0181880 A1    Jul. 28, 2011

Related U.S. Application Data

(60) Provisional application No. 60/780,542, filed on Mar. 9, 2006.

(51) Int. Cl.
*G01N 21/47* (2006.01)
*F16L 9/14* (2006.01)

(52) U.S. Cl.
USPC ............................ 356/337; 356/338; 138/140

(58) Field of Classification Search
USPC ......... 356/335–338, 432–437, 244; 428/36.3, 428/36.6, 36.7, 36.8, 36.9, 36.91; 425/35.9; 301/124.1, 137, 125; 138/140
See application file for complete search history.

(56) References Cited

U.S. PATENT DOCUMENTS

| | | | |
|---|---|---|---|
| 2,880,357 A | 3/1959 | Snow et al. | 315/5.23 |
| 2,978,799 A | 4/1961 | Benteler | 29/183.5 |

(Continued)

FOREIGN PATENT DOCUMENTS

| | | | |
|---|---|---|---|
| EP | 0613881 | 9/1994 | C07C 231/08 |
| EP | 0655629 | 11/1994 | G01R 33/30 |

(Continued)

OTHER PUBLICATIONS

Development of a *Ginkgo biloba* fingerprint chromatogram with UV and evaporative light scattering detection and optimization of the evaporative light scattering detector operating conditions by Van Nederkassel AM et al; Journal of Chromatography A, Elsevier, Amsterdam NL vol. 1805, No. 2, Sep. 2, 2005, pp. 230-239, XP004984428, ISSN: 0021-9673.

(Continued)

*Primary Examiner* — Sang Nguyen
(74) *Attorney, Agent, or Firm* — Beverly J. Artale

(57) ABSTRACT

Components suitable for use in an evaporative light scattering detector and other devices are disclosed. Methods of making and using components suitable for use in an evaporative light scattering detector and other devices are also disclosed.

19 Claims, 9 Drawing Sheets

(56) References Cited

U.S. PATENT DOCUMENTS

| | | | |
|---|---|---|---|
| 3,297,905 A | 1/1967 | Fiedor et al. | 315/3.5 |
| 3,318,340 A * | 5/1967 | Torti, Jr. | 138/140 |
| 3,426,420 A * | 2/1969 | Grant et al. | 228/130 |
| 3,504,195 A | 3/1970 | Kimball et al. | 307/243 |
| 3,807,173 A * | 4/1974 | Zmuda et al. | 60/302 |
| 3,877,817 A | 4/1975 | Ralston | 356/180 |
| 4,059,405 A | 11/1977 | Sodickson | 23/230 |
| 4,059,712 A * | 11/1977 | Bothwell | 428/34.6 |
| 4,070,111 A | 1/1978 | Harrick | 356/83 |
| 4,159,523 A | 6/1979 | Neer | 364/571 |
| 4,185,369 A * | 1/1980 | Darrow et al. | 29/889.722 |
| 4,207,364 A * | 6/1980 | Nyberg | 138/141 |
| 4,213,703 A | 7/1980 | Haunold et al. | 356/244 |
| 4,249,291 A * | 2/1981 | Grondahl et al. | 29/889.722 |
| 4,333,597 A * | 6/1982 | Hardwick | 228/108 |
| 4,397,557 A | 8/1983 | Herwig et al. | 356/342 |
| 4,484,061 A | 11/1984 | Zelinka et al. | 219/301 |
| 4,518,700 A | 5/1985 | Stephens | 436/52 |
| 4,565,447 A | 1/1986 | Nelson | 356/319 |
| 4,781,456 A | 11/1988 | Nogami | 356/51 |
| 4,823,168 A | 4/1989 | Kamahori et al. | 356/246 |
| 4,827,435 A | 5/1989 | Marron et al. | 364/559 |
| 4,848,904 A | 7/1989 | Sapp et al. | 356/319 |
| 4,922,309 A | 5/1990 | Sekiwa et al. | 356/300 |
| 4,929,078 A | 5/1990 | Harmon | 356/320 |
| 4,931,660 A | 6/1990 | Mayer et al. | 250/575 |
| 5,029,276 A | 7/1991 | Buehler et al. | 250/208.2 |
| 5,134,276 A | 7/1992 | Hobbs | 250/208.2 |
| 5,376,783 A | 12/1994 | Vecht et al. | 250/208.2 |
| 5,434,412 A | 7/1995 | Sodickson et al. | 250/343 |
| 5,540,825 A | 7/1996 | Yeung et al. | 204/452 |
| 5,628,891 A | 5/1997 | Lee | 204/612 |
| 5,680,209 A | 10/1997 | Machler | G01J 3/02 |
| 5,742,200 A | 4/1998 | He | 329/320 |
| 5,745,243 A | 4/1998 | Wilcox et al. | 356/419 |
| 5,745,293 A | 4/1998 | Lassalle | 359/614 |
| 5,983,709 A | 11/1999 | O'Keefe | 73/53.02 |
| 6,002,477 A | 12/1999 | Hammer | 356/307 |
| 6,004,639 A * | 12/1999 | Quigley et al. | 428/36.3 |
| 6,040,914 A | 3/2000 | Bortz et al. | 356/435 |
| 6,090,280 A | 7/2000 | Conelly et al. | 210/198.2 |
| 6,091,494 A | 7/2000 | Kreikebaum | 356/336 |
| 6,097,034 A | 8/2000 | Weckstrom et al. | 250/495.1 |
| 6,106,710 A | 8/2000 | Fischer et al. | 210/198.2 |
| 6,108,083 A | 8/2000 | Machler | 356/328 |
| 6,122,055 A | 9/2000 | O'Donohue et al. | 356/338 |
| 6,148,661 A | 11/2000 | Dreux | 73/61.52 |
| 6,151,113 A | 11/2000 | O'Donoghue et al. | 356/338 |
| 6,175,409 B1 | 1/2001 | Nielsen et al. | 356/337 |
| 6,207,369 B1 | 3/2001 | Wohlstadter | 435/6 |
| 6,210,571 B1 | 4/2001 | Zambias et al. | 210/198.2 |
| 6,229,605 B1 | 5/2001 | Benedict | 356/339 |
| 6,243,170 B1 | 6/2001 | Ershov | 356/519 |
| 6,249,348 B1 | 6/2001 | Jung et al. | 356/319 |
| 6,260,407 B1 | 7/2001 | Petro et al. | 73/61.52 |
| 6,297,505 B1 | 10/2001 | Frandsen et al. | 250/339.12 |
| 6,345,528 B2 | 2/2002 | Petro et al. | 73/61.52 |
| 6,362,880 B1 | 3/2002 | Anderson, Jr. et al. | 356/337 |
| 6,406,632 B1 | 6/2002 | Safir et al. | 210/656 |
| 6,411,383 B1 | 6/2002 | Wyatt | 356/338 |
| 6,426,006 B1 | 7/2002 | Zambias | 210/659 |
| 6,449,040 B1 | 9/2002 | Fujita | 356/319 |
| 6,454,947 B1 | 9/2002 | Safir et al. | 210/656 |
| 6,461,515 B1 | 10/2002 | Safir et al. | 210/656 |
| 6,475,391 B2 | 11/2002 | Safir et al. | 210/656 |
| 6,497,631 B1 * | 12/2002 | Fritzke et al. | 473/566 |
| 6,511,850 B1 | 1/2003 | Vigh et al. | 436/127 |
| 6,577,392 B1 | 6/2003 | Nielsen et al. | 356/338 |
| 6,595,049 B1 | 7/2003 | Maginnis, Jr. et al. | 73/202.5 |
| 6,651,009 B1 | 11/2003 | Trainoff et al. | 702/23 |
| 6,717,179 B1 * | 4/2004 | Yamazaki et al. | 257/59 |
| 6,730,228 B2 | 5/2004 | Petro et al. | 210/656 |
| 6,741,348 B2 | 5/2004 | Larsen et al. | 356/319 |
| 6,809,819 B1 | 10/2004 | Vinjamoori et al. | 356/337 |
| 6,855,258 B2 | 2/2005 | Petro et al. | 210/656 |
| 6,857,452 B2 * | 2/2005 | Quigley et al. | 138/125 |
| 6,866,786 B2 | 3/2005 | Petro et al. | 210/656 |
| 6,908,557 B2 | 6/2005 | Chordia et al. | 210/659 |
| 6,936,174 B2 | 8/2005 | Dreux et al. | 210/659 |
| 7,006,218 B2 | 2/2006 | Anderson, Jr. et al. | 356/337 |
| 2001/0027949 A1 | 10/2001 | Safir et al. | 210/635 |
| 2001/0037674 A1 | 11/2001 | Petro et al. | 73/61.52 |
| 2002/0063097 A1 | 5/2002 | Fukunaga et al. | 210/656 |
| 2002/0119271 A1 * | 8/2002 | Quigley et al. | 428/36.9 |
| 2002/0121468 A1 | 9/2002 | Fischer et al. | 210/198.2 |
| 2002/0170976 A1 | 11/2002 | Bergh et al. | 236/49.1 |
| 2002/0174713 A1 | 11/2002 | Petro et al. | 73/61.52 |
| 2002/0177563 A1 | 11/2002 | Griffin et al. | 514/42 |
| 2003/0066803 A1 | 4/2003 | Wright | 210/656 |
| 2003/0070988 A1 | 4/2003 | Petro et al. | 210/656 |
| 2003/0080062 A1 | 5/2003 | Petro et al. | 210/656 |
| 2003/0086092 A1 | 5/2003 | Gangloff et al. | 356/437 |
| 2003/0089663 A1 | 5/2003 | Petro et al. | 210/656 |
| 2003/0210465 A1 | 11/2003 | Valenti | 359/614 |
| 2004/0000046 A1 * | 1/2004 | Stinson | 29/426.4 |
| 2004/0018118 A1 | 1/2004 | Waki | 422/70 |
| 2004/0025575 A1 | 2/2004 | Petro et al. | 73/61.55 |
| 2004/0026222 A1 | 2/2004 | Adachi | 200/512 |
| 2004/0132688 A1 | 7/2004 | Griffin et al. | 514/54 |
| 2004/0163948 A1 | 8/2004 | Fukunaga et al. | 204/228.7 |
| 2004/0200777 A1 | 10/2004 | Dreux et al. | 210/656 |
| 2004/0214341 A1 | 10/2004 | Fedorova | 436/139 |
| 2005/0148838 A1 | 7/2005 | Gamache et al. | 600/407 |
| 2005/0240385 A1 | 10/2005 | Xie et al. | 703/11 |
| 2005/0258087 A1 | 11/2005 | Chordia et al. | 210/198.2 |
| 2005/0277199 A1 | 12/2005 | Isbell et al. | 436/161 |
| 2006/0093769 A1 * | 5/2006 | Biebuyck | 428/36.91 |
| 2008/0143174 A1 * | 6/2008 | Burkett | 301/126 |

FOREIGN PATENT DOCUMENTS

| | | | | |
|---|---|---|---|---|
| EP | 1380329 | 1/2004 | | B01D 15/08 |
| EP | 1471351 | 10/2004 | | G01N 30/86 |
| GB | 824137 | 11/1959 | | |
| WO | 03036258 | 5/2003 | | |
| WO | 03081208 | 10/2003 | | |
| WO | 2004077047 | 9/2004 | | G01N 30/74 |
| WO | 2006083511 | 8/2006 | | G01B 9/02 |

OTHER PUBLICATIONS

SofTA Evaproative Light Scattering Detector [online]; Jul. 19, 2004, pp. 1-2 XP002461689; Chrom Tech Inc by Anonymous.

Double Beam Laser Absorption Spectroscopy: Shot Noise-Limited Performance at Baseband with Novel Electronic Noise Canceller, SPIE, vol. 1435, Optical Methods for Ultrasensitive Detection and Analysis: Techniques and Applications by Kurt L. Haller and Philip C.D. Hobbs (1991), pp. 298-309.

OceanOptics Product Catalog, 2003.

* cited by examiner

EVAPORATIVE LIGHT SCATTERING DETECTOR

CROSS REFERENCE TO RELATED APPLICATION

This application claims the benefit of U.S. Patent Application Ser. No. 60/780,542 filed Mar. 9, 2006.

FIELD OF THE INVENTION

The present invention is directed to a variety of components suitable for use in analytical devices such as an evaporative light scattering detector (ELSD). The present invention is also directed to methods of making and using a variety of components such as in an evaporative light scattering detector (ELSD) device.

BACKGROUND OF THE INVENTION

There is a need in the art for various components suitable for use in analytical devices, such as an evaporative light scattering detector (ELSD), so as to provide improved device performance.

SUMMARY OF THE INVENTION

The present invention addresses some of the difficulties and problems discussed above by the discovery of components suitable for use in analytical devices including, but not limited to, an evaporative light scattering detector (ELSD). The components of the present invention provide one or more advantages over known components used in analytical devices. The one or more advantages may include, but are not limited to, the ability to provide a more stable processing temperature along a length of a tubular member, such as a drift tube; the ability to monitor and/or adjust a processing temperature along a length of a tubular member, such as a drift tube; the ability to effectively and efficiently adjust flow properties through a tubular member, such as a drift tube; the ability to effectively and efficiently disassemble components in order to clean individual components; and the ability to amplify an inputted voltage signal so as to provide an output voltage that has a voltage component that is independent of the gain applied to the input voltage signal.

In one exemplary embodiment, the component of the present invention comprises a composite tubular member comprising a tubular wall structure having a first end, a second end, an inner wall surface facing an interior of the tubular wall structure, and an outer wall surface, the tubular wall structure comprising an inner layer of a first metal and an outer layer of a second metal, the second metal having a higher coefficient of heat transfer compared to the first metal. The inner layer may comprise, for example, stainless steel, while the outer layer may comprise, for example, copper.

In another exemplary embodiment, the component of the present invention comprises a tubular member comprising a tubular wall structure having a first end, a second end, a length L, an inner wall surface facing an interior of the tubular wall structure, and an outer wall surface; two or more temperature sensors positioned along a length L of the tubular wall structure; and a heating element positioned over the outer wall surface along length L of the tubular wall structure. In one desired embodiment, the heating element is able to maintain an average temperature gradient of less than about 8° C. along length L. The tubular member may further comprise one or more heating elements positioned over the outer wall surface along length L of the tubular wall structure.

The present invention is further directed to a cartridge/impactor assembly suitable for use with a drift tube and an evaporative light scattering detector, wherein the cartridge/impactor assembly comprises (1) a cartridge comprising (i) a cartridge insert that is sized so as to be extendable within a first end of a drift tube along an inner wall surface of the drift tube and (ii) an impactor positioning member along a length of the cartridge insert, the impactor positioning member being capable of temporarily securing an impactor within the cartridge insert so as to occupy a portion of a cross-sectional flow area through the cartridge insert; and (2) at least one optional impactor sized so as to be positionable within the cartridge insert via the impactor positioning member. In one desired embodiment, the impactor is one impactor belonging to a set of impactors of varying sizes and geometries, which are interchangeable within the cartridge insert so that a cross-sectional flow area through the cartridge insert can be adjusted. For example, the set of impactors may be designed so as to occupy from between about 25% and about 75% of the total cross-sectional flow area through the cartridge insert.

The present invention is also directed to a cartridge suitable for positioning one or more optional impactors in one or more stationary positions within a drift tube, the cartridge comprising (i) a cartridge insert that is sized so as to be extendable within a first end of a drift tube along an inner wall surface of the drift tube, and (ii) at least one impactor positioning member along a length of the cartridge insert, the impactor positioning member being capable of temporarily securing an impactor within the cartridge insert so that the impactor occupies a portion of a cross-sectional flow area through the cartridge insert. As discussed above, the cartridge may comprise one impactor belonging to a set of impactors, wherein the set of impactors comprises two or more impactors having a variety of different impactor sizes, each impactor within the set of impactors being removably attachable to the cartridge insert via the impactor positioning member so as to occupy a portion of a cross-sectional flow area through the cartridge insert.

The present invention is even further directed to an electronic circuit comprising a voltage amplifier capable of providing a voltage gain to an inputted voltage signal; an output resistor in series with the voltage amplifier; a current source providing a constant current to the output resistor; and a current steering diode in series with the current source, the current steering diode providing one-way flow of constant current from the current source to the output resistor; the electronic circuit being capable of providing an output voltage comprising a voltage offset component that is independent of amplifier gain provided by the voltage amplifier. The electronic circuit may be used in combination with additional electronic components, one or more external system components, or both.

The present invention is also directed to methods of making and using one or more of the above-described components of the present invention. One or more of the above-described components of the present invention may be used to perform an analytical test method step or steps, such as a method of analyzing a test sample that potentially contains at least one analyte. In one exemplary embodiment, the method comprises introducing a test sample into a tubular member comprising a tubular wall structure having a length L, a first end, a second end, an inner wall surface facing an interior of the tubular wall structure, and an outer wall surface, the tubular member being at least partially surrounded by a heating element; and maintaining an interior of the tubular wall structure at a temperature so that the interior has an average temperature gradient along length L of less than about 8° C. In some embodiments, the method comprises maintaining an interior of the tubular wall structure at a temperature so that the interior has an average temperature gradient along length L of as low as about 1.5° C.

The present invention is even further directed to methods of using the above-described electronic circuit of the present invention to process an inputted voltage signal. In one exemplary embodiment, the method comprises the steps of providing an inputted voltage signal; amplifying the inputted voltage signal via a voltage amplifier; and converting the inputted voltage signal into an output voltage comprising a voltage offset component that is independent of amplifier gain provided by the voltage amplifier. The exemplary method may be performed within an electronic system containing one or more additional electronic components, wherein at least one of the additional electronic components cannot process a negative input voltage. The exemplary method may also be performed within a system containing one or more external system components, wherein a negative input voltage negatively impacts an output of at least one of the external system components.

These and other features and advantages of the present invention will become apparent after a review of the following detailed description of the disclosed embodiments and the appended claims.

DETAILED DESCRIPTION OF THE INVENTION

Figure 1:
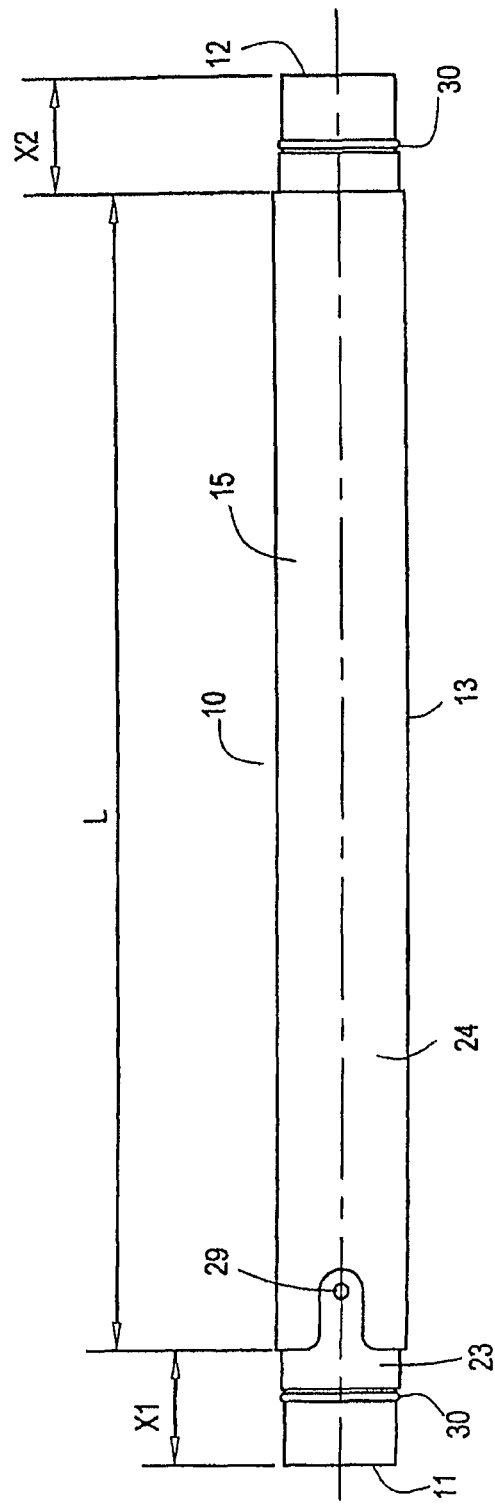
FIG. 1 depicts an exemplary composite tubular member of the present invention.

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

The present invention is directed to a variety of components suitable for use in analytical devices including, but not limited to, an evaporative light scattering detector (ELSD) apparatus, a charged aerosol detector (e.g., Corona CAD) apparatus, and a mass spectrometer. In one desired embodiment of the present invention, one or more of the disclosed components are incorporated into an evaporative light scattering detector (ELSD) apparatus. A description of suitable evaporative light scattering detectors (ELSD) and components used therein may be found in, for example, U.S. Pat. Nos. 6,229,605 and 6,362,880, the subject matter of both of which is hereby incorporated herein by reference in their entirety.

The present invention is further directed to methods of making a variety of components suitable for use in analytical devices, such as an ELSD apparatus. The present invention is even further directed to methods of using one or more of the disclosed components in an analytical device, such as in an evaporative light scattering detector (ELSD) device, in order to contribute to the performance of one or more functions of the device.

In one exemplary embodiment, one or more of the disclosed components of the present invention (shown in FIGS. 1-9) are incorporated into an ELSD apparatus. For example, a tubular member of the present invention, such as exemplary tubular member 10 (shown in FIGS. 1-5), may be combined with a nebulizer 52 (shown in FIG. 5), and other ELSD apparatus components, in order to provide an improved drift tube for the ELSD apparatus. In another example, a cartridge/impactor assembly of the present invention, such as exemplary cartridge/impactor assembly 51 (shown in FIGS. 5-6), may be used in combination with a conventional drift tube or exemplary tubular member 10 of the present invention to provide "split-flow" capabilities to an ELSD apparatus. In yet a further example, an electronic circuit of the present invention, such as exemplary electronic circuit 80 (shown in FIG. 9), may be incorporated into an analytical device, such as an ELSD apparatus, in order to provide beneficial processing of one or more inputted voltage signals within the device.

As shown in FIGS. 1-9, the various components of the present invention comprise a number of individual component features. A description of various components, possible component features, and various component configurations is provided below.

I. Device Components

The present invention is directed to the following individual components, which may be used alone or in combination with one another to contribute to the performance of known analytical devices.

A. Tubular Member

Figure 4:
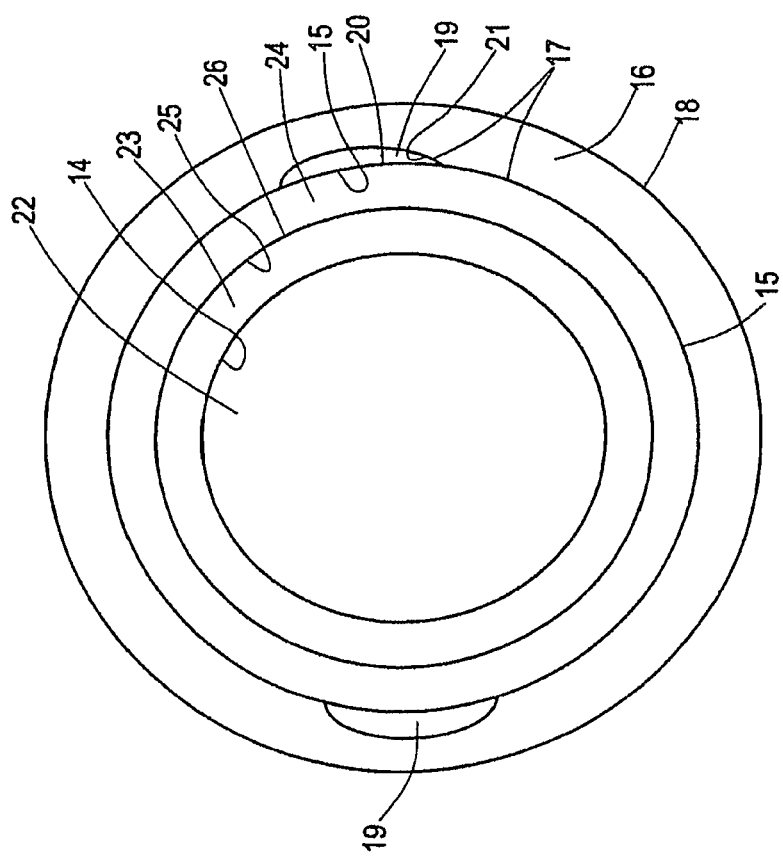
FIG. 4 depicts a cross-sectional view of the exemplary composite tubular member shown in FIG. 3 along line A-A.

The present invention is directed to tubular members such as exemplary tubular member 10 shown in FIGS. 1 and 4. The tubular members of the present invention may be used as a drift tube in an ELSD apparatus or as a tubular member in any other analytical device (e.g., in a charged aerosol detector (e.g., Corona CAD) apparatus or a mass spectrometer).

As shown in FIGS. 1 and 4, exemplary tubular member 10 comprises a first end 11; a second end 12; a tubular wall structure 13 extending a distance between first end 11 and second end 12; and an interior 22 (shown in FIG. 4) surrounded by tubular wall structure 13.

1. Tubular Wall Structure

Exemplary tubular member 10 comprises a tubular wall structure 13 having one or more concentric layers. Each of the one or more concentric layers may provide a desired feature (e.g., structural integrity, high temperature resistance, etc.) to the resulting tubular member 10. Further, each of the one or more concentric layers has a layer thickness and is formed from one or more layer materials in order to provide specific features (e.g., chemical inertness, etc.) to the resulting tubular member 10.

Tubular wall structure 13 may further comprise attachment features 30 proximate first end 11 and second end 12. Attachment features 30 may be used to connect exemplary tubular member 10 to one or more components of a given device. Suitable attachment features 30 include, but are not limited to, threads so that exemplary tubular member 10 can be attached to corresponding threads on one or more components of a given device; a flange (not shown) containing one or more holes therein so that exemplary tubular member 10 can be attached to one or more components of a given device via bolts or screws extending through the one or more holes; one or more holes within tubular wall structure 13 at first end 11 and/or second end 12 so that exemplary tubular member 10 can be attached to one or more components of a given device via bolts or screws extending into the one or more holes (see, for example, holes 45 in first end 11 of tubular wall structure 13 shown in FIG. 5); and a clamping member that can be used to attach exemplary tubular member 10 to one or more components of a given device via corresponding clamping members.

In one exemplary embodiment (discussed below), tubular wall structure 13 comprises two or more concentric layers. In one desired embodiment, tubular wall structure 13 comprises an inner layer 23 and an outer layer 24 (shown in FIG. 4), wherein inner layer 23 provides a majority of the overall structural integrity to tubular member 10, and outer layer 24 provides additional properties, such as insulating properties, to inner layer 23.

a. Inner Layer

In one exemplary embodiment, tubular wall structure 13 comprises one or more inner layers or inner sleeves 23 in combination with one or more outer layers 24. As illustrated in FIGS. 1-4, inner layer 23 typically extends an entire length of tubular member 10 (e.g., the sum of lengths L+X1+X2 as shown in FIG. 1). Further, inner layer 23 typically forms first end 11, second end 12, and inner wall surface 14 surrounding interior 22 of tubular member 10.

Inner layer 23 comprises an inner wall surface 14, which faces interior 22 of tubular wall structure 13. Inner layer 23 also comprises outer surface 25, which may be in direct contact with an inner surface 26 of outer layer 24. In one desired embodiment, outer surface 25 of inner layer 23 is in direct contact with inner surface 26 of outer layer 24.

In one exemplary embodiment, inner layer 23, or at least inner wall surface 14 of inner layer 23, comprises an inert material. Suitable inert materials include, but are not limited to, metals such as aluminum, stainless steel and titanium; polymeric materials such as polyetheretherketone (PEEK), and polytetrafluoroethylene (PTFE); glasses including borosilicate glass; and ceramic materials. In one exemplary embodiment, inner wall surface 14 comprises a metal selected from aluminum and stainless steel. In a further exemplary embodiment, inner wall surface 14 comprises 6061-T6 aluminum or 316L stainless steel, desirably, 316L stainless steel.

Inner layer 23 may have an average layer thickness that varies depending on a number of factors including, but not limited to, the materials used to form inner layer 23, the presence or absence of one or more outer layers, and the desired structural requirements of tubular member 10 (e.g., the desired pressure capacity of exemplary tubular member 10). Typically, inner layer 23 has an average layer thickness of from about 0.25 millimeters (mm) (0.01 inches (in)) to about 50.8 mm (2 in). In one desired embodiment, inner layer 23 comprises stainless steel and has an average layer thickness of from about 0.76 mm (0.03 in) to about 1.52 mm (0.6 in). In a further desired embodiment, inner layer 23 comprises stainless steel and has a thickness from about 2.54 mm (0.10 in) to about 5.08 mm (0.20 in) (more desirably, about 3.30 mm (0.13 in)).

b. Outer Layer

Tubular wall structure 13 may optionally comprise one or more layers in addition to the inner layer(s) 23 described above. As illustrated in FIG. 1, outer layer or outer sleeve 24 may extend over a portion of inner layer 23. Alternatively, outer layer or outer sleeve 24 may extend over substantially a complete outer surface area of inner layer 23. As shown in FIG. 4, outer layer 24 has an inner surface 26, which may be in contact with outer surface 25 of inner layer 23. In other embodiments, there may be a desired spacing between inner surface 26 of outer layer 24 and outer surface 25 of inner layer 23.

In one exemplary embodiment, outer layer 24 comprises a material that provides good heat conductive properties to exemplary tubular member 10. For example, outer layer 24 may comprise a metal, such as copper, so that when heat is applied to outer wall surface 15 of outer layer 24, outer layer 24 provides a substantially uniform amount of heat along outer surface 25 of inner layer 23. This exemplary embodiment is particularly useful when tubular member 10 is utilized as a drift tube in an ELSD apparatus.

In a further exemplary embodiment, outer layer 24 comprises an insulating material that provides insulative properties to exemplary tubular member 10 (e.g., inner layer 23 of exemplary tubular member 10). For example, outer layer 24 may comprise foam insulation, such as polyurethane foam, so as to insulate inner layer 23. This exemplary embodiment is particularly useful when tubular member 10 is utilized as a drift tube in an ELSD apparatus.

Outer layer 24 may comprise a variety of materials depending on a number of factors including, but not limited to, the desired function of the outer layer, the thickness of the outer layer, etc. Suitable materials for forming outer layer 24 include, but are not limited to, metals such as copper, polymeric foam materials such as a polyurethane foam, glass materials, and ceramic materials. In one desired embodiment, outer layer 24 comprises a layer of copper electroplated to inner layer 23, such as an inner layer 23 formed from stainless steel. In a further exemplary embodiment, outer layer 24 comprises a preformed sleeve of copper fitted over an inner layer 23, such as an inner layer 23 formed from stainless steel.

Typically, outer layer 24 has an average layer thickness of from about 0.10 mm (0.004 in) to about 50.8 mm (2 in). In one exemplary embodiment, outer layer 24 comprises a copper layer and has an average layer thickness of about 0.76 mm (0.03 in) to about 1.52 mm (0.6 in). In one desired embodiment, outer layer 24 comprises a copper layer and has a thickness from about 2.54 mm (0.10 in) to about 7.62 mm (0.30 in) (more desirably, about 6.35 mm (0.25 in)).

In a further exemplary embodiment, tubular wall structure 13 may further comprise an optional outermost clear coat material (not shown) applied over a portion of or substantially all of outer surface 15 so as to provide, for example, enhanced chemical resistance. The clear coat material may comprise any clear coat material including, but not limited to, polyurethane materials. Typically, when present, the clear coat layer has an average layer thickness of from about 0.01 to about 0.5 mm.

c. Tubular Wall Structure Cross-Sectional Shape

Tubular wall structure 13 has an inlet cross-sectional flow area at first end 11, an outlet cross-sectional flow area at second end 12 of tubular wall structure 13, and a tubular cross-sectional flow area between first end 11 and second end 12. In one exemplary embodiment of the present invention, the tubular cross-sectional flow area is substantially equal to the inlet cross-sectional flow area, the outlet cross-sectional flow area, or both. In a further exemplary embodiment of the present invention, the tubular cross-sectional flow area is substantially equal to both the inlet cross-sectional flow area and the outlet cross-sectional flow area.

Each of the tubular cross-sectional flow area, the inlet cross-sectional flow area and the outlet cross-sectional flow area may have any desired cross-sectional configuration. Suitable cross-sectional configurations include, but are not limited to, circular, rectangular, square, pentagon, triangular, and hexagonal cross-sectional configurations. In one desired embodiment, each of the tubular cross-sectional flow area, the inlet cross-sectional flow area, and the outlet cross-sectional flow area has a circular cross-sectional flow area.

d. Tubular Member Dimensions

The tubular members of the present invention may have a variety of sizes depending on the use of the tubular member. For example, when the tubular member of the present invention is to be used as a drift tube in an ELSD apparatus, the tubular member typically has an overall length of up to about 50.8 cm (20 in), and more typically, within a range of about 20.32 cm (8 in) to about 40.64 cm (16 in). In one desired embodiment, the tubular member of the present invention is used as a drift tube in an ELSD apparatus, and has an overall length of about 27.94 cm (11 in). However, it should be understood that there is no limitation on the overall dimensions of the disclosed tubular members.

As described above, tubular wall structure 13 may have a tubular cross-sectional flow area, an inlet cross-sectional flow area, and an outlet cross-sectional flow area. Each of the tubular cross-sectional flow area, the inlet cross-sectional flow area, and the outlet cross-sectional flow area may vary in size depending on the use of a given tubular wall structure. Typically, each of the tubular cross-sectional flow area, the inlet cross-sectional flow area, and the outlet cross-sectional flow area is independently up to about 506 cm$^2$ (78.5 in$^2$). In one desired embodiment, the tubular member of the present invention is used as a drift tube in an ELSD apparatus, and each of the tubular cross-sectional flow area, the inlet cross-sectional flow area, and the outlet cross-sectional flow area is about 3.84 cm$^2$ (0.59 in$^2$). However, as mentioned above, there is no limitation on the overall dimensions of the disclosed tubular members.

e. Pressure Capacity

Tubular members and cartridges of the present invention may be constructed from materials in order to withstand an internal pressure that varies depending on the end use of a given component. Typically, tubular members and cartridges of the present invention are constructed to have a pressure capacity of up to about 15,000 psig. In some embodiments, tubular members and cartridges of the present invention are constructed to have a pressure capacity ranging from about 500 to about 5,000 psig.

2. Temperature Sensors

Figure 2:
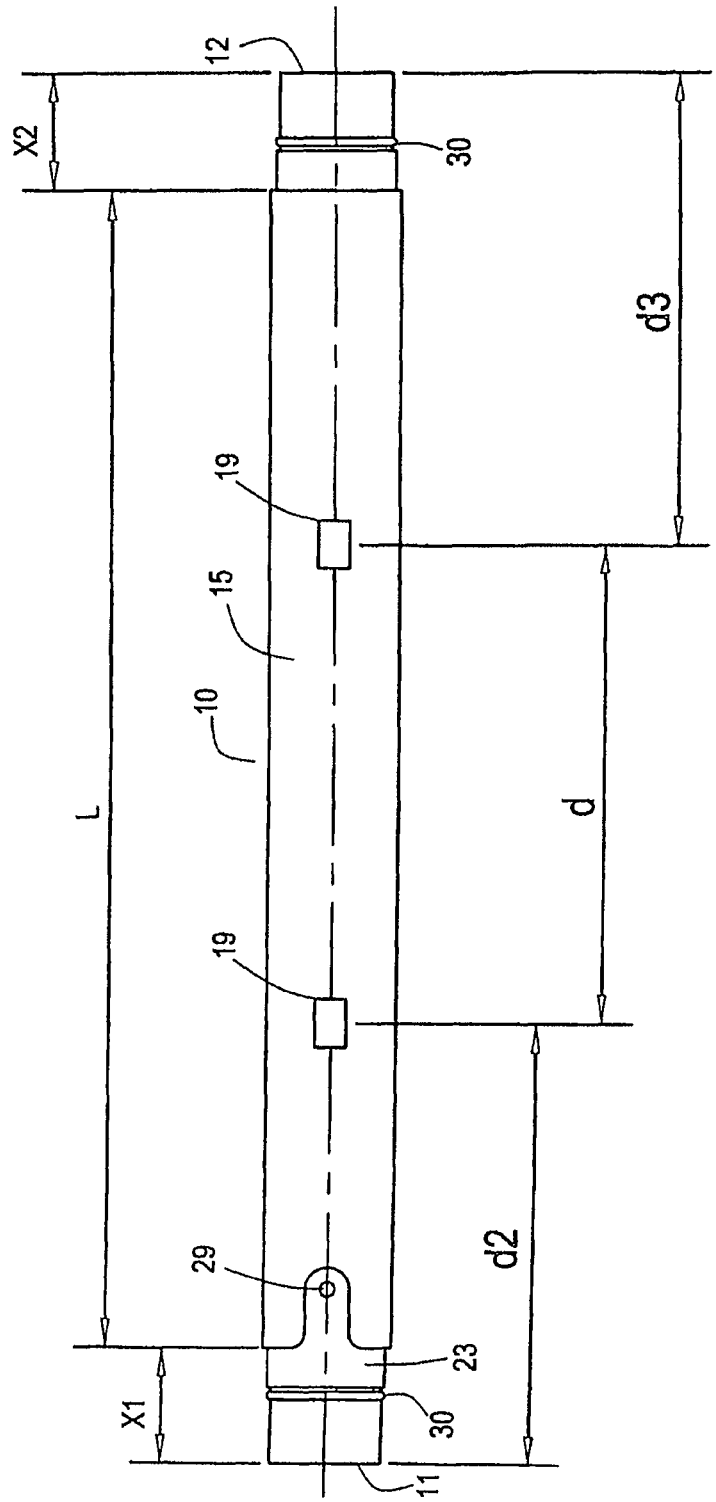
FIG. 2 depicts a view of the exemplary composite tubular member shown in FIG. 1 with multiple sensors thereon.

The tubular members of the present invention may further comprise one or more temperature sensors, such as exemplary temperature sensors 19, positioned along a length of the tubular member. As shown in FIGS. 2 and 4, exemplary tubular member 10 comprises two sensors 19; however, it should be understood that any number of sensors may be positioned along exemplary tubular member 10.

Typically, when present, two or more temperature sensors 19 are positioned along a length of exemplary tubular member 10. Each temperature sensor 19 may be positioned along outer surface 15 of exemplary tubular member 10, along outer surface 25 of inner layer 23, or both.

When two or more temperature sensors 19 are used, it is desirable for temperature sensors 19 to be distributed along a substantial portion of the length of exemplary tubular member 10. As shown in FIG. 2, distance d is a distance between temperature sensors 19 while distance d2 represents a distance between first end 11 and one temperature sensor 19, and d3 represents a distance between second end 12 and another temperature sensor 19. In one exemplary embodiment, temperature sensors 19 are separated from one another by a distance of about L/2, where distance L is a length of tubular wall structure 13. Desirably, two or more temperature sensors 19 are positioned along tubular wall structure 13 in order to measure the temperature and any temperature gradient along tubular wall structure 13.

Figure 3:
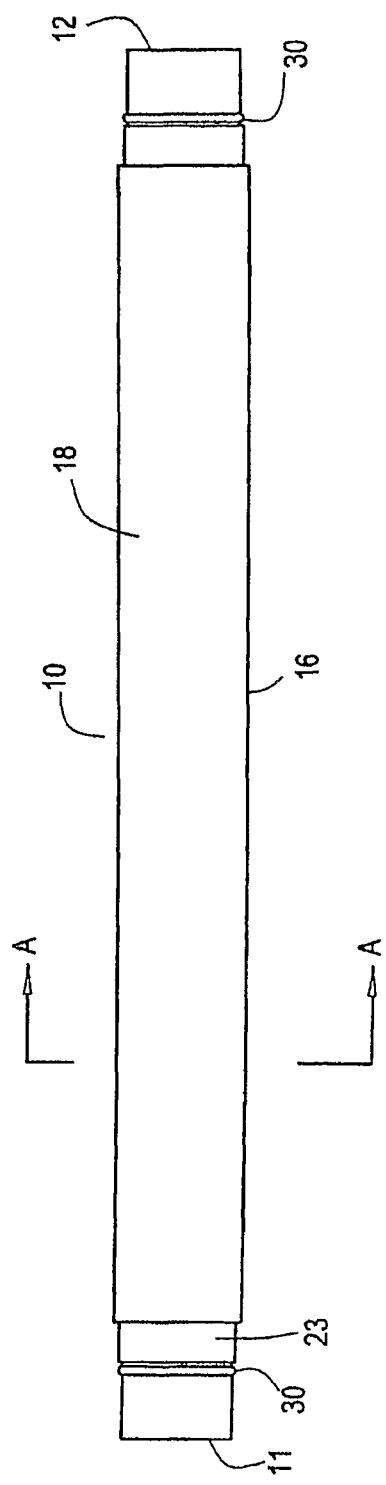
FIG. 3 depicts a view of the exemplary composite tubular member shown in FIG. 2 with a heating element positioned over the multiple sensors.

As shown in FIG. 4, which is a cross-sectional view along line A-A of FIG. 3, sensor inner surface 20 of temperature sensor 19 may be positioned in contact with outer wall surface 15 of outer layer 24 or in other alternate locations in and around interior 22 (not shown). FIG. 4 also illustrates that temperature sensor outer surface 21 may be in contact with an inner surface 17 of optional heating element 16 described below).

One benefit of using multiple temperature sensors 19 is to be able to accurately measure the temperature in various locations throughout and along tubular wall structure 13 and, in concert with one or more heating elements 16 discussed below, to provide better heating control of tubular wall structure 13 in order to provide more reproducible results and better performance. In one desired embodiment, x temperature sensors may be positioned in, around, or on tubular wall structure 13 such that the sensors are spaced apart, for example, by an equal distance d, though sensors 19 may of course be spaced at any distance from each other or along tubular wall structure 13. When x temperature sensors 19 are spaced an equal distance d from each other, tubular wall structure 13 is desirably split into a number of zones equal to (x+1) so as to monitor a temperature along tubular wall structure 13 and control and/or minimize the amount of temperature variation along tubular wall structure 13. Alternatively, when exemplary tubular member 10 comprises x temperature sensors, the x temperature sensors are desirably positioned a distance of about L/(x−1) from one another along tubular wall structure 13.

Desirably, the tubular members of the present invention comprise a tubular wall structure that enables a minimal average temperature gradient along a length L of the tubular wall structure. In one exemplary embodiment, the tubular member of the present invention comprises a tubular wall structure that enables an average temperature gradient along length L of less than about 8° C. In one desired embodiment, the tubular member comprises a tubular wall structure that enables an average temperature gradient along length L of less than about 7° C. (or less than about 6° C., or less than about 5° C., or less than about 4° C., or less than about 3° C., or less than about 2° C., or less than about 1.5° C., or less than about 1.0° C.).

3. Heating Elements

Tubular members of the present invention may further comprise one or more optional heating elements such as exemplary heating element 16 shown in FIGS. 3-4. As shown in FIGS. 3-4, exemplary heating element 16 comprises an inner surface 17 and an outer surface 18. Although illustrated as a single, continuous heating element, exemplary heating element 16 may comprise one or more heat sources including, but not limited to, heating tape, point contacts, and a heated blanket or sleeve, such as exemplary heating element 16. Further, although exemplary heating element 16 is shown in FIG. 3 to be positioned over outer wall surface 15 along a length of tubular wall structure 13, exemplary heating element 16 may be sized and positioned so as to extend along an entire length of tubular wall structure 13 or only a portion of an entire length of tubular wall structure 13.

A number of commercially available heating elements may be used in the present invention. Suitable commercially available heating elements include, but are not limited to, silicon rubber heating elements commercially available from Tempco Electric Heater Corporation (Wood Dale, Ill.) under the trade designation Silicon Rubber Heaters, KAPTON® Flexible Heaters commercially available from Tempco Electric Heater Corporation (Wood Dale, Ill.), and other heating products, such as tapes and sheaths, commercially available from Tempco Electric Heater Corporation (Wood Dale, Ill.).

In one desired embodiment, four silicon rubber heating elements commercially available from Tempco Electric Heater Corporation (Wood Dale, Ill.) under the trade designation Silicon Rubber Heaters are used to heat tubular wall structure 13. The silicon rubber heating elements are adhesively attached and distributed along outer surface 15 of exemplary tubular member 10, along outer surface 25 of inner layer 23, or both depending on the construction of tubular wall structure 13.

In another desired embodiment, one or more heating elements 16 are used in concert with one or more temperature sensors 19 in order to produce an average temperature gradient along length L of tubular member 10 of less than about 8° C. In a further desired embodiment, one or more heating elements 16 are used in concert with one or more temperature sensors 19 in order to produce an average temperature gradient along length L of tubular member 10 of less than about 7° C. (or less than about 6° C., or less than about 5° C., or less than about 4° C., or less than about 3° C., or less than about 2° C., or less than about 1.5° C., or less than about 1.0° C.).

4. Grounding Screw

Tubular members of the present invention may further comprise one or more grounding screws such as exemplary grounding screw 29 shown in FIG. 1. Exemplary grounding screw 29 enables electrical grounding of exemplary tubular member 10.

B. Cartridge/Impactor Assembly

The present invention is further directed to newly designed cartridges, impactors, and cartridge/impactor assemblies as shown in FIGS. 5-8B. The disclosed cartridges, impactors, and cartridge/impactor assemblies are particularly useful as removable components in an ELSD apparatus.

Figure 5:
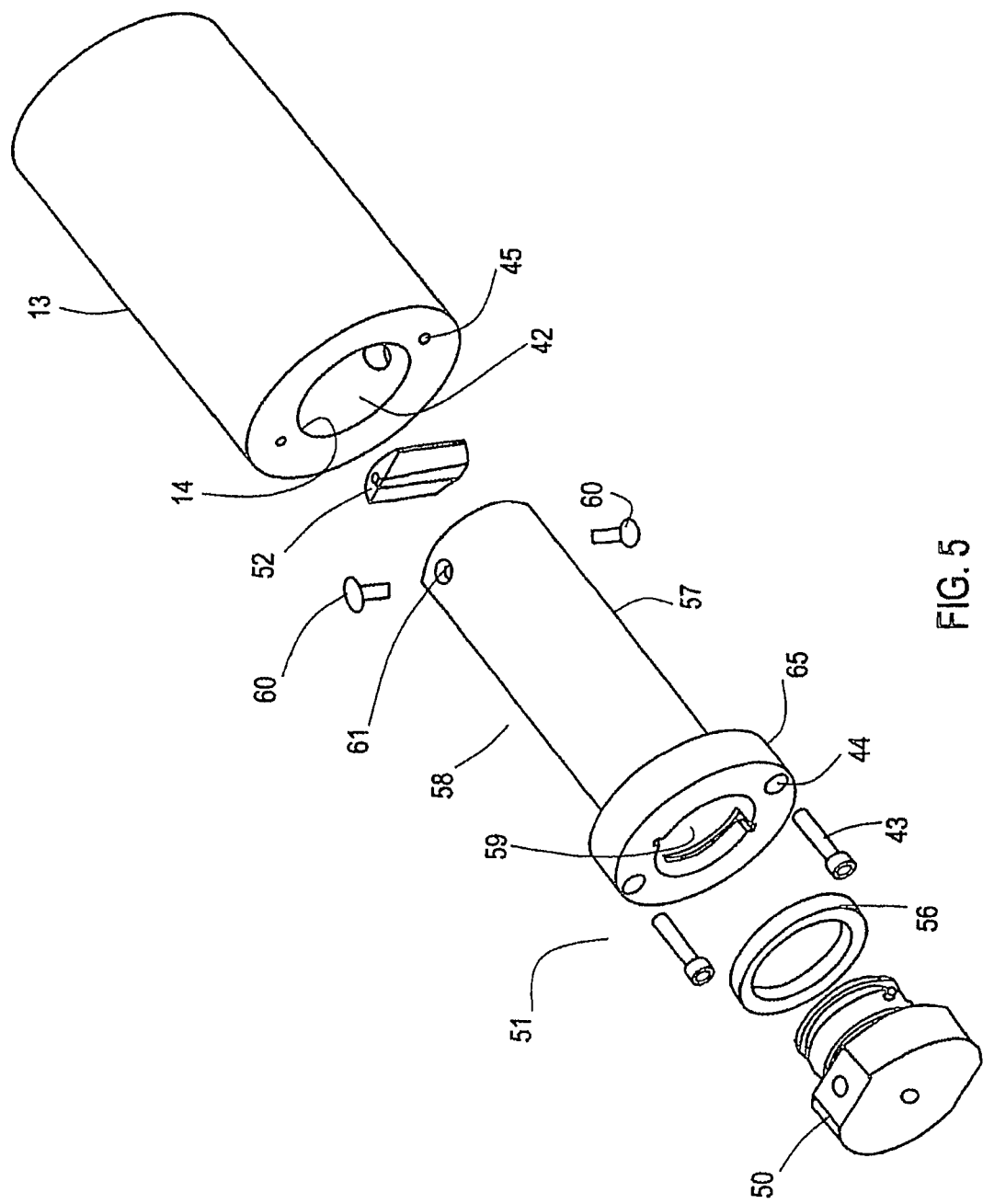
FIG. 5 depicts an exemplary cartridge/impactor assembly of the present invention.

In one exemplary embodiment shown in FIG. 5, exemplary removable cartridge/impactor assembly 51 comprises exemplary removable cartridge 58 in combination with impactor 52. Exemplary removable cartridge/impactor assembly 51 is shown in combination with the following additional device components: nebulizer 50, O-ring 56, screws 43 suitable for attaching exemplary removable cartridge 58 to tubular wall structure 13.

1. Cartridges

Figure 6:
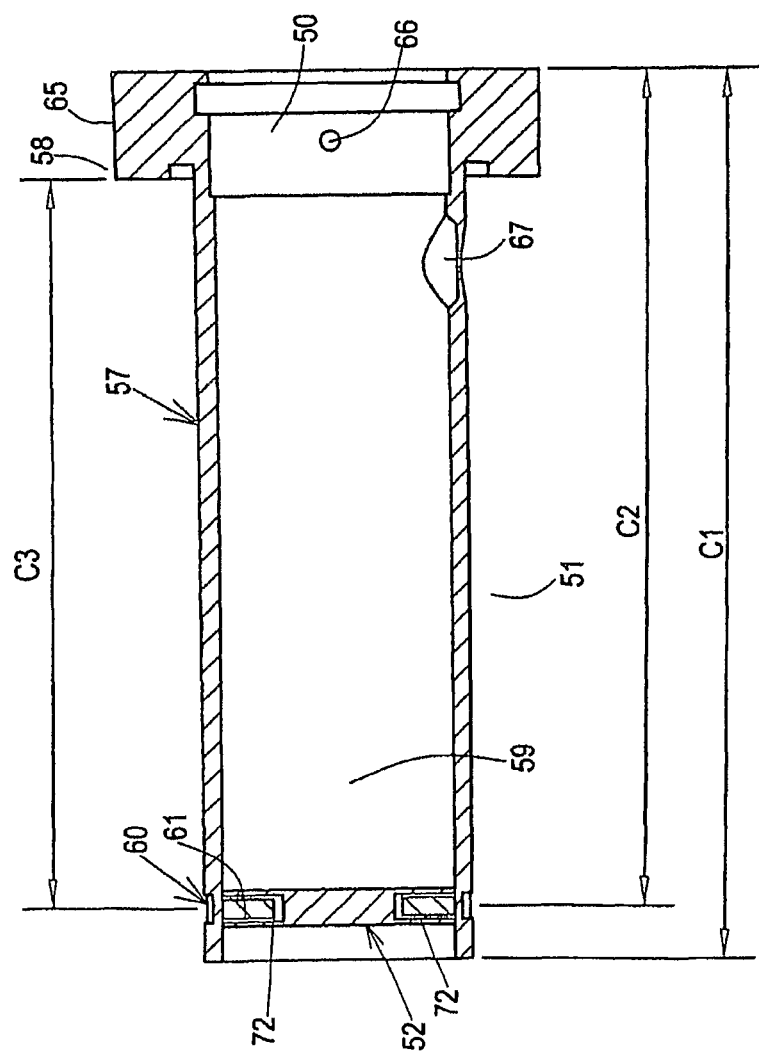
FIG. 6 depicts a cross-sectional view of the exemplary cartridge/impactor assembly shown in FIG. 5.

Exemplary cartridge 58 shown in FIGS. 5-6 comprises cartridge insert 57, flange section 65, and one or more impactor positioning members 61 capable of temporarily securing one or more impactors (e.g., exemplary impactor 52) within cartridge insert 57 so that the impactor(s) occupies a portion of a cross-sectional flow area through cartridge insert 57.

In one exemplary embodiment, the cartridge is suitable for positioning one or more impactors in a stationary position(s) within a drift tube of an ELSD apparatus. In this exemplary embodiment, the cartridge comprises (i) a cartridge insert that is sized so as to be extendable within a first end of a drift tube (e.g., first end 11) along an inner wall surface (e.g., inner wall surface 14) of the drift tube, and (ii) one or more impactor positioning members positioned along a length of the cartridge insert, each of the one or more impactor positioning members being capable of temporarily securing an impactor within the cartridge insert so that the impactor occupies a portion of a cross-sectional flow area through the cartridge insert.

The cartridges of the present invention may be sized so as to be suitable for use with any of the above-described tubular members, including exemplary tubular member 10. Cartridge insert 57 is sized so as to be extendable within an opening 42 at first end 11 of tubular wall structure 13 along inner wall surface 14 of tubular wall structure 13, i.e., within a drift tube. As shown in FIG. 5, cartridge insert 57 may be positioned between nebulizer 50 and tubular wall structure 13 such that nebulizer 50 may be removably attached to cartridge/impactor assembly 51 by screws 43 or by any other attachment member. Similarly, cartridge/impactor assembly 51 may be removably attached to tubular wall structure 13 by any suitable attachment member, including, but not limited to, screws 43 suitable for being received by holes 44 within flange 65 of exemplary cartridge 58 and then by holes 45 in tubular wall structure 13.

Exemplary cartridge 58 may further comprise one or more impactor positioning members 61 (shown as screw holes 61 in FIGS. 5 and 6). Each impactor positioning member 61 is positioned within cartridge insert 57 so as to removably secure impactor 52 in place along a length C3 of cartridge insert 57 so as to occupy a portion of a cross-sectional flow area 59 through cartridge insert 57. As shown in FIG. 5, exemplary impactor positioning members 61 along with corresponding screws 60 are used to position impactor 52 within cartridge insert 57. Although exemplary cartridge 58 comprises one set of opposing impactor positioning members 61, it should be understood that two or more sets of opposing impactor positioning members 61 may be positioned along a length of cartridge insert 57 so as to provide flexibility in the position of impactor 52 within cartridge insert 57.

As shown in FIG. 6, impactor 52 is positioned a length C3 from flange 65 of exemplary cartridge 58. It should be noted that length C3 can vary depending on a number of factors including, but not limited to, the overall length (e.g., C1) of cartridge insert 57, the overall length of a corresponding tubular member, the desired position of impactor 52, and the test sample composition to be tested. For example, the ratio of length C3 to length C1 may be lower than what is shown in FIG. 6 so as to enable positioning of impactor 52 based on the needs of a particular test sample.

It should be further noted that the overall length, C1, of exemplary cartridge 58 can vary depending on a number of factors including, but not limited to, the overall length of a corresponding tubular member, the desired position of impactor 52 relative to the overall length of a corresponding tubular member, and the test sample composition to be tested. In one exemplary embodiment, C1 may be as long as inner layer 23 such that cartridge insert 57 effectively acts as an inner surface layer of a tubular wall structure of a corresponding tubular member. Typically, C1 is less than half the length of a corresponding tubular member, and more typically from about 25% to 33% of the length of a corresponding tubular member. In one exemplary embodiment, exemplary cartridge 58 has an overall length of about 8.10 centimeters (cm) (3.19 in), a set of impactor positioning members (e.g., impactor positioning members 61) positioned about 7.62 cm (3.00 in) within a tubular member having an overall length of about 27.94 cm (11.00 in).

As further discussed below, it is desirable for impactor 52 to be removable such that impactors having various dimensions can be removably interchanged so that a wide range of sample types and mobile phases can be tested within a given tubular member simply by substituting an appropriately sized impactor 52. By changing or even removing impactor 52 altogether, a given device may be converted from a first "split flow" configuration having a first cross-sectional flow area (e.g., 50% of the total cross-sectional flow area of cartridge insert 57) to a second "split flow" configuration having a second cross-sectional flow area (e.g., 25% of the total cross-sectional flow area of cartridge insert 57) to a single flow configuration (e.g., 100% of the total cross-sectional flow area of cartridge insert 57) in which impactor 52 is removed altogether. In a split flow configuration, the size of impactor 52 can be varied in order to change the amount of the split for maximum optimization, depending on the mobile phase and samples to be detected. Further, the removable impactor also allows for easy access to tubular wall structure 13 for cleaning purposes (e.g., when tubular wall structure 13 is utilized as a drift tube in an ELSD apparatus).

As noted above, although not shown in FIGS. 5-6, exemplary cartridge 58 may comprise two or more sets of impactor positioning members positioned along a length of the cartridge insert in order to optionally position two or more impactors within the cartridge insert. The multiple sets of impactor positioning members provide enhanced flexibility to a user when deciding between a single flow configuration or any number of possible "split flow" configurations within the same cartridge.

As shown in FIGS. 5-6, exemplary cartridge 58 may further comprise flange 65 suitable for connecting exemplary cartridge 58 to other device components, such as a tubular member, a gasket, an O-ring, a filter, an end cap, etc. In one desired embodiment, flange 65 is used to connect exemplary cartridge 58 to a tubular member, such as exemplary tubular member 10 described above, so as to form a drift tube for use in an ELSD apparatus.

In one embodiment of the present invention, flange 65 is formed as an integral part of exemplary cartridge 58. Such a configuration is shown in exemplary cartridge/impactor assembly 51 shown in FIGS. 5-6. In other embodiments, flange 65 may be a separate cartridge component that is fixed onto one end of cartridge insert 57. Regardless of construction, flange 65 comprises one or more structural features so as to enable flange 65 to be connected to any other apparatus component. Suitable structural features include, but are not limited to, bolts extending from a surface of the flange, threaded holes within the flange, pipe threads, compression fittings, connectors, etc.

Cartridge 58 may comprise one or more materials, desirably one or more inert materials. Suitable materials for forming cartridge 58 include, but are not limited to, metals such as aluminum, stainless steel and titanium; polymeric materials such as polyetheretherketone (PEEK), and polytetrafluoroethylene (PTFE); glasses including borosilicate glass; and ceramic materials. In one exemplary embodiment of the present invention, cartridge 58 comprises a metal selected from aluminum and stainless steel. In a desired embodiment, cartridge 58 comprises stainless steel such as 316L stainless steel.

Cartridge insert 57 of cartridge 58 may have an average wall thickness that varies depending on a number of factors including, but not limited to, the inner diameter of a given tubular member, the desired structural integrity of cartridge insert 57, etc. Typically, cartridge insert 57 has an average wall thickness of from about 0.10 mm (0.004 in) to about 50.8 mm (2 in). In one exemplary embodiment, cartridge insert 57 comprises stainless steel and has an average wall thickness of about 2.54 mm (0.10 in) to about 10.16 mm (0.40 in) (more desirably, about 6.35 mm (0.25 in)).

2. Impactors

As shown in FIGS. 5-6, exemplary removable cartridge/impactor assembly 51 further comprises one or more impactors 52. Two exemplary impactors 52 are shown in FIGS. 7A-8B. Desirably, each impactor 52 comprises a planar, solid body 73 having major surfaces 74 bound by upper and lower peripheral surfaces 70, and side peripheral surfaces 71. Within upper and lower peripheral surfaces 70 are positioned openings 72 suitable for receiving a corresponding impactor positioning member 61 of cartridge insert 57 or a corresponding attachment member (e.g., a screw) capable of engaging with upper or lower peripheral surface 70 and a corresponding impactor positioning member 61.

In one exemplary embodiment of the present invention, a set of interchangeable impactors 52 is designed to be removable insertable and mounted within a cartridge insert 57 of a given cartridge 58. Desirably, the set of impactors include a plurality of impactors sized so as to provide various percentages of a total cross-sectional flow area 59 through cartridge insert 57. For example, a given set of impactors 52 may be capable of occupying from about 5% to about 95% of a total cross-sectional flow area 59 through cartridge insert 57. Other sets of impactors 52 may be capable of occupying any percent of a total cross-sectional flow area 59 through cartridge insert 57 ranging from about 5% to about 95% of the total cross-sectional flow area.

The various impactors 52 may be dimensioned as desired so as to fit within a given cartridge insert. In one exemplary embodiment, impactors 52 have a width (I1) of from about 5.0 mm (0.2 in) to about 25.4 mm (1.0 in), a length (I2) of from about 5.0 mm (0.2 in) to about 25.4 mm (1.0 in), and a thickness (I3) of from about 1.3 mm (0.05 in) to about 25.4 mm (1.0 in). (see FIGS. 7A-B). In one desired embodiment, impactors 52 have a width (I1) of about 14.0 mm (0.55 in), a length (I2) of about 21.8 mm (0.86 in), and a thickness (I3) of about 3.2 mm (0.125 in).

Figure 7A:
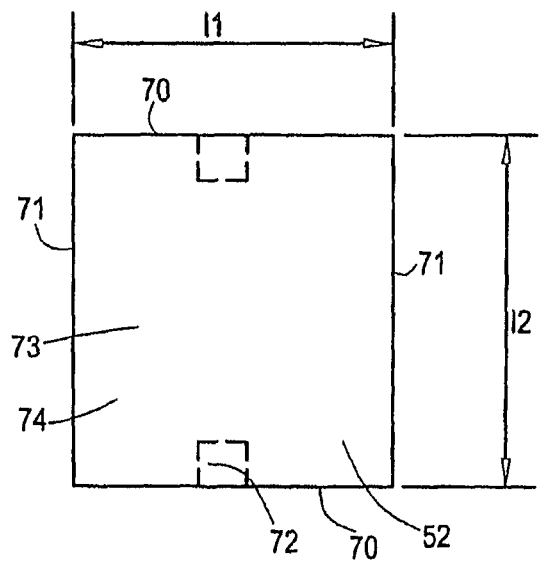
FIGS. 7A-7B depict frontal and side views respectively of a first exemplary impactor suitable for use with the cartridge/impactor assembly shown in FIGS. 5-6.
Figure 7B:
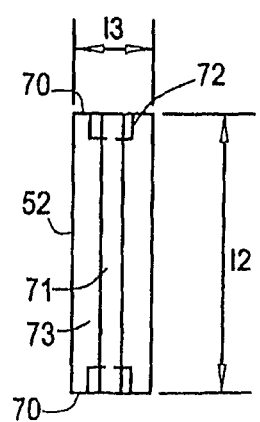
Figure 8A:
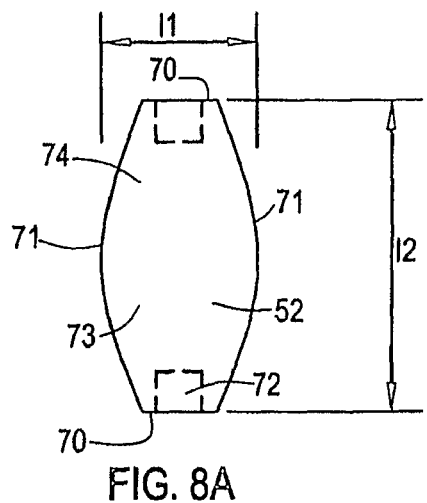
FIGS. 8A-8B depict frontal and side views respectively of a second exemplary impactor suitable for use with the cartridge/impactor assembly shown in FIGS. 5-6.
Figure 8B:
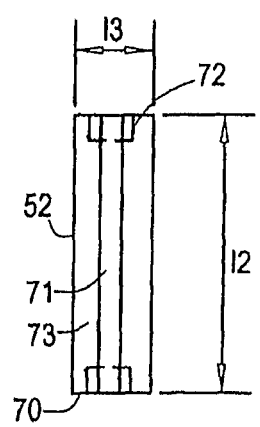

Additionally, the shape of impactors 52 may vary as desired. As shown in FIGS. 7A-7B, first exemplary impactor 52 has a substantially rectangular shape. As shown in FIGS. 8A-8B, second exemplary impactor 52 has a substantially oblong shape. Other suitable shapes for impactor 52 include, but are not limited to, a circular shape, a square shape, a triangular shape, a spherical shape, etc. The only limitation on the shape of a given impactor is for the shape to provide a sufficient impact surface area for a given nebulized mobile phase.

Impactors 52 may comprise one or more materials, desirably one or more inert materials. Suitable materials for forming impactors 52 include, but are not limited to, metals such as aluminum, stainless steel and titanium; polymeric materials such as polyetheretherketone (PEEK), and polytetrafluoroethylene (PTFE); glasses including borosilicate glass; ceramic materials; or combinations thereof. In one exemplary embodiment of the present invention, impactors 52 comprise a metal selected from aluminum and stainless steel optionally coated with TEFLON® material. In a desired embodiment, impactors 52 comprise stainless steel, such as 316L stainless steel, coated with TEFLON® material.

3. Impactor Attachment Members

Impactors 52 may be removably attached to cartridge insert 57 by any suitable attachment member including, but not limited to, one or more screws 60 as shown in FIGS. 5 and 6. As shown in FIG. 5, one or more screws 60 may be inserted through corresponding impactor positioning members 61 of cartridge insert 57 so as to extend through a sidewall of cartridge insert 57 and into a respective opening 72 within impactor 52 as shown in FIG. 6.

C. Electronic Circuitry

The present invention is further directed to electronic circuitry suitable for use in analytical devices. The electronic circuitry of the present invention comprises electronic circuitry capable of amplifying one or more inputted voltage signals so as to produce an output voltage comprising a voltage offset component that is independent of amplifier gain provided by a voltage amplifier. In one exemplary embodiment, the electronic circuitry comprises a voltage amplifier capable of providing a voltage gain to an inputted voltage signal; an output resistor in series with the voltage amplifier; a current source providing a constant current to the output resistor; and a current steering diode in series with the current source, the current steering diode providing one-way flow of constant current from the current source to the output resistor; wherein the electronic circuitry is capable of providing an output voltage comprising a voltage offset component that is independent of amplifier gain provided by the voltage amplifier. Exemplary electronic circuitry of the present invention is shown in FIG. 9.

Figure 9:
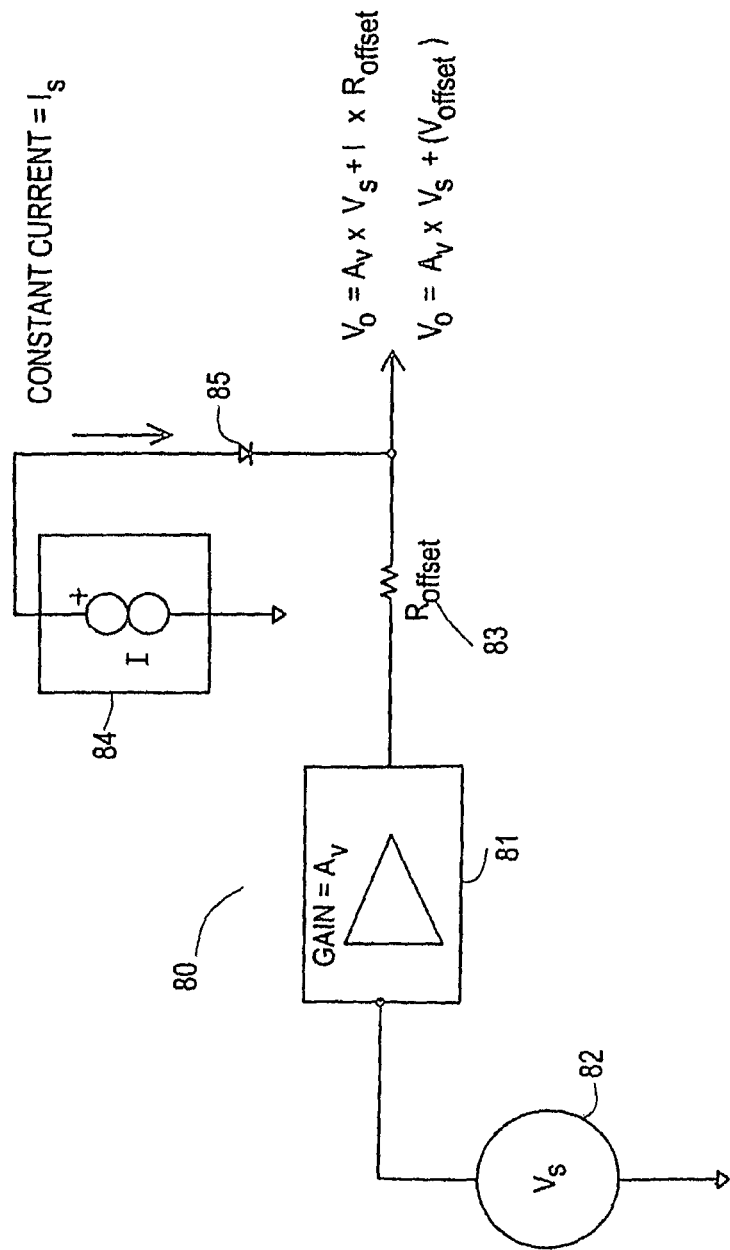
FIG. 9 provides a schematic diagram of an electronic circuit of the prior art suitable for use in devices such as an evaporative light scattering detector (ELSD) device.

As shown in FIG. 9, exemplary electronic circuitry 80 comprises voltage amplifier 81 capable of providing a voltage gain to an inputted voltage signal 82 from a device such as a photodetector (not shown). Exemplary electronic circuitry 80 also comprises output resistor 83 in series with voltage amplifier 81, a current source 84 providing a constant current ($I_s$) to output resistor 83, and a current steering diode 85 in series with current source 84. Current steering diode 85 provides one-way flow of constant current ($I_s$) from current source 84 to output resistor 83.

In exemplary electronic circuitry 80, an output voltage, $V_o$, may be provided by formula:

$$V_o = (V_s \times \text{Gain}) + (I_s \times R_{\mathit{offset}}) = V_s \times \text{Gain} + (V_{\mathit{offset}})$$

wherein $V_s$ is the inputted voltage signal; "Gain" is the voltage gain; $I_s$ is the constant current provided to the output resistor; $R_{\mathit{offset}}$ is a resistance of the output resistor; and $V_{\mathit{offset}}$ is the voltage offset component that is independent of the voltage gain.

Exemplary electronic circuitry 80 may be used in connection with devices, which process voltage signals having a voltage magnitude of up to about 2500 mV. Typically, exemplary electronic circuitry 80 is used in connection with devices so that the inputted voltage signal has a voltage ranging from about 0 to about 2500 mV; the voltage gain is a multiple ranging from about 0.1 to about 16; the constant current to the output resistor ranges from about 100 µA to about 2.0 mA; the output resistor has a resistance ranging from about 2000 to about 5.0 ohms; and the voltage offset component has a voltage ranging from about 100 µV to about 50 mV. In one desired embodiment, exemplary electronic circuitry 80 is used in connection with devices so that the inputted voltage signal has a voltage ranging from about 1500 to about 2500 mV (more desirably, about 2000 mV); the voltage gain is a multiple ranging from about 1 to about 16; the constant current to the output resistor ranges from about 100 µA to about 1.0 mA; the output resistor has a resistance ranging from about 200 to about 5 ohms (more desirably, about 10 ohms); and the voltage offset component has a voltage ranging from about 100 µV to about 20 mV (more desirably, about 10 mV).

The electronic circuitry of the present invention, such as exemplary electronic circuitry 80, may be used in combination with additional electronic components, one or more external system components, or both. In particular, the electronic circuitry of the present invention is useful in systems that contain one or more electronic components that cannot process a negative input voltage. For example, many electronic systems capable of performing an analog-to-digital conversion have moved away from using devices that process both positive (+) and negative (−) input voltages, and instead only process positive (+) input voltages.

The electronic circuitry of the present invention is also particularly useful in systems that contain one or more external system components, wherein a negative input voltage negatively impacts an output of at least one of the external system components. For example, integrators that function to trace output of a chromatography detector vs. time and subsequently perform a mathematical operation of integration on the peak areas of detector responses to enumerate total analyzed sample at 100%, as well as individual peak responses as some percentage of the 100% total, cannot in some cases handle a negative input voltage due to the potential of the negative input voltage to be interpreted as a negative peak component (e.g., the negative input voltage would be summed with positive input voltages so as to reduce a given individual peak response).

In one desired embodiment of the present invention, the electronic circuitry is used to process an inputted voltage signal, wherein the inputted voltage signal comprises a voltage signal from a photodetector. In a further desired embodiment of the present invention, the electronic circuitry is a component in an evaporative light scattering detector.

II. Methods of Making Components

The present invention is also directed to methods of making the above-described components of the present invention. Each of the above-described components may be prepared using conventional techniques. For example, in one exemplary method of making a tubular member, the method may comprise forming a first layer or first sleeve 23 from an inert material (e.g., stainless steel) using a metal casting process step, and surrounding outer surface 25 of inner layer 23 with an outer layer 24. Outer layer 24 may be coated onto outer surface 25 of inner layer 23 using, for example, a metal sputtering step, or may be preformed using a molding or casting step, and subsequently fitted over inner layer 23. Metal casting steps may also be used to form cartridge 58 and impactors 52. If any of these components comprise a polymeric material, any conventional thermoforming step (e.g., injection molding, cast molding, etc.) may be used to form the component.

III. Methods of Using Components

The present invention is also directed to methods of using one or more of the above-described components in an analytical device, such as an ELSD apparatus.

A. Methods of Analyzing a Test Sample

One or more of the above-described components may be used in an analytical device, such as an ELSD apparatus, in order to analyze a test sample. In one exemplary embodiment, the method comprises a method of analyzing a test sample that potentially contains at least one analyte, wherein the method comprises the steps of introducing the test sample into a tubular member comprising a tubular wall structure having a length L, a first end, a second end, an inner wall surface facing an interior of the tubular wall structure, and an outer wall surface, the tubular member being at least partially surrounded by a heating element; and maintaining an interior of the tubular wall structure at a temperature so that the interior has an average temperature gradient along length L of less than about 8° C. (or less than about 7° C., or less than about 6° C., or less than about 5° C., or less than about 4° C., or less than about 3° C., or less than about 2° C., or less than about 1.5° C., or less than about 1.0° C.). In one desired embodiment, the method utilizes a tubular wall structure comprising an inner layer of a first metal (e.g., stainless steel) and an outer layer of a second metal (e.g., copper), wherein the second metal has a higher coefficient of heat transfer compared to the first metal. In this exemplary method, the tubular member may be utilized as a drift tube in an ELSD apparatus.

The exemplary method of analyzing a test sample may also utilizing a tubular member having two or more temperature sensors positioned along length L of the tubular wall structure.

In a further exemplary embodiment, the method of analyzing a test sample comprises utilizing a tubular member (e.g., as a drift tube) in combination with a cartridge so as to enable quick conversion from a split-flow configuration to a single-flow configuration and vice versa. In this exemplary embodiment, the method may comprise utilizing a cartridge comprising (i) a cartridge insert that is sized so as to be extendable within a first end of the tubular member along an inner wall surface of the tubular member, and (ii) one or more impactor positioning members along a length of the cartridge insert, each of the impactor positioning members being capable of temporarily securing an optional impactor within the cartridge insert so as to occupy a portion of a cross-sectional flow area through the cartridge insert. The tubular member may further comprise at least one impactor sized so as to be positionable within the cartridge insert via the one or more impactor positioning members.

The above exemplary methods of analyzing a test sample may further comprise any of the following step: nebulizing the test sample to form an aerosol of particles within a mobile phase; optionally removing a portion of the particles prior to introducing the test sample into the tubular member (e.g., the drift tube); evaporating a portion of the mobile phase along length L of the tubular member; directing a light beam at the remaining particles so as to scatter the light beam; detecting the scattered light; and analyzing data obtained in the detecting step.

Typically, data obtained in the above-described method is in the form of a voltage signal that provides an indication of the amount of analyte, if any, present in a test sample. The electronic circuitry of the present invention may be used to further process the voltage signals obtained in the above-described exemplary method.

B. Method of Processing an Input Voltage Signal

In a further embodiment, the present invention is directed to methods of processing an input voltage signal from one electronic component in an electronic system. In one exemplary embodiment, the method of processing an inputted voltage signal comprising the steps of providing an inputted voltage signal; amplifying the inputted voltage signal via a voltage amplifier; and converting the inputted voltage signal into an output voltage comprising a voltage offset component that is independent of amplifier gain provided by the voltage amplifier.

The step of converting the inputted voltage signal into an output voltage may produce an output voltage, $V_o$, as provided in formula (I) described above. In one exemplary embodiment, in order to produce a desired voltage offset component having a voltage ranging from about 500 μV to about 2.0 mV with an inputted voltage signal having a voltage ranging from about 0 to about 2000 mV, the voltage amplifier provides a voltage gain comprising a multiple ranging from about 1 to about 16, the output resistor has a resistance ranging from about 2000 to about 5.0 ohms, and the constant current provided to the output resistor ranges from about 100 μA to about 2.0 mA.

The method of processing an inputted voltage signal is particularly useful for converting an inputted voltage signal into an output voltage within an electronic system containing one or more additional electronic components, wherein at least one of said additional electronic components cannot process a negative input voltage. The method of processing an inputted voltage signal is also particularly useful for converting an inputted voltage signal into an output voltage within a system containing one or more external system components, wherein a negative input voltage negatively impacts an output of at least one of said external system components as described above.

In one desired embodiment, the method of processing an inputted voltage signal comprises a method of processing an inputted voltage signal from a photodetector. In a further desired embodiment, the method of processing an inputted voltage signal comprises a method of processing an inputted voltage signal within an evaporative light scattering detector.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Preparation of a Tubular Wall Structure Suitable for Use as a Drift Tube

A tubular member comprising stainless steel (type 316) was formed during a die casting process (the "inner layer"). The resulting tubular member had an overall length of 28.24 cm (11.12 in) (e.g., L+X1+X2 as shown in FIG. 1), wherein L=24.13 cm (9.5 in) and X1=X2=2.06 cm (0.81 in), a circular cross-sectional configuration with an inner diameter of 2.21 cm (0.87 in), and an outer diameter of 2.54 cm (1.00 in).

A preformed copper sleeve (the "outer layer") was then fitted around the inner layer so as to cover about 24.13 cm (9.5 in) of the stainless steel inner layer as shown in FIG. 1. The copper sleeve had an inner diameter of 2.54 cm (1.00 in) and an outer diameter of 3.18 cm (1.25 in).

The resulting tubular wall structure had an overall wall thickness of 9.65 mm (0.38 in), and a pressure capacity of about 5000 psig.

EXAMPLE 2

Preparation of a Tubular Member Having Multiple Sensors

The tubular member formed in Example 1 was further processed in order to incorporate multiple temperature sensors into the tubular member. Two sensors were adhesively placed on an outer wall surface of the tubular wall structure (e.g., on an outer surface of the copper outer layer). The sensors were spaced approximately 8.26 cm (3.25 in) (length d2 and length d3) from either end of the tubular wall structure as illustrated in FIG. 2.

EXAMPLE 3

Preparation of a Tubular Member Having Multiple Heating Elements and Sensors

The tubular member formed in Example 2 was further processed in order to combine a heating element with the tubular member. Four silicone rubber heating elements positioned within a heating sheet were positioned over the two sensors and an outer surface of the copper outer layer as illustrated in FIG. 3. The heater sheet length was 24.13 cm (9.5 in) and situated directly onto the copper outer layer.

EXAMPLE 4

Temperature Gradient Data Along Tubular Members

The tubular member of Example 3 was compared with a second tubular member without the outer copper layer. Temperature readings were taken at several locations along each of the tubular wall structures. The testing was conducted using a Next Generation ELSD Prototype: 45 C/1.5 L/min/ Impactor On/Gain 16 with a mobile phase of 100% $H_2O$ @ 3.0 mL/rnin. Fluke 54II Thermometer temperature sensors 19 were placed at four locations on the two respective tubular wall structures and 500 data points were taken for each zone (with each data point being timed at 5 seconds). The first sensor/zone was positioned closest to first end 11, the second sensor/zone next, then the third sensor/zone, and finally, the fourth sensor/zone was positioned nearest second end 12. Table 1 below summarizes the results of the temperature profile for the tubular member comprising only stainless steel, while Table 2 summarizes the results of the temperature profile for the tubular member comprising the copper-encased tubular wall structure.

TABLE 1

Summary of Temperature Profile Results For Tubular Member Comprising a Single Layer of Stainless Steel

| | Stainless Steel Tubular Wall Structure/Drift Tube Stainless Steel Drift Tube | | | |
|---|---|---|---|---|
| | Zone 1 | Zone 2 | Zone 3 | Zone 4 |
| AVE: | 40.9 | 51.0 | 44.8 | 42.6 |
| STD DEV: | 0.035 | 0.156 | 0.305 | 0.215 |
| % RSD: | 0.09 | 0.31 | 0.68 | 0.51 |
| MAX: | 41.0 | 51.4 | 45.8 | 43.2 |
| MIN: | 40.9 | 50.6 | 44.4 | 42.3 |
| MAX – MIN: | 0.1 | 0.8 | 1.4 | 0.9 |

Average Temperature Gradient Over 4 Zones: 10.1° C.

TABLE 2

Summary of Temperature Profile Results For Tubular Member Comprising a Two-Layer Structure Comprising an Inner Layer of Stainless Steel and an Outer Layer of Copper

| | Copper-Encased Tubular Wall Structure/Drift Tube Copper-Encased Drift Tube | | | |
|---|---|---|---|---|
| | Zone 1 | Zone 2 | Zone 3 | Zone 4 |
| AVE: | 44.7 | 46.2 | 45.4 | 44.6 |
| STD DEV: | 0.068 | 0.069 | 0.147 | 0.191 |
| % RSD: | 0.15 | 0.15 | 0.32 | 0.43 |
| MAX: | 44.8 | 46.3 | 45.8 | 45.1 |
| MIN: | 44.5 | 46 | 45.1 | 44.3 |
| MAX – MIN: | 0.3 | 0.3 | 0.7 | 0.8 |

Average Temperature Gradient Over 4 Zones: 1.6° C.

EXAMPLE 5

Preparation of a Cartridge/Impactor Assembly Suitable for Use With a Drift Tube

The tubular member formed in Example 1 was further processed in order to incorporate a cartridge/impactor assembly as shown in FIGS. 5-6. The length of the cartridge (C1) was 3.19 in. and length C2=3.00 in. The outer diameter of the cartridge insert was 22.1 mm (0.87 in) while the inner diameter was 15.7 mm (0.62 in).

A first impactor from a set of impactors had a width I1 of 14.0 mm (0.55 in), a length I2 of 15.7 mm (0.62 in), and a thickness I3 of 3.2 mm (0.125 in) (see FIGS. 7A-8B). A second impactor from the set of impactors had a width I1 of 7.6 mm (0.3 in), a length I2 of 15.7 mm (0.62 in), and a thickness I3 of 3.2 mm (0.125 in). The impactors are held in placed by screws extending through the cartridge insert and into side walls of the impactors.

EXAMPLE 6

Preparation of a Cartridge/Impactor Assembly Suitable for Use With a Drift Tube

A cartridge/impactor assembly similar to the cartridge/impactor assembly of Example 5 was formed except that the cartridge had a cartridge length C3 substantially equal to the midsection length L of the drift tube formed in Example 1.

EXAMPLE 7

Preparation of an Electronic Circuit Suitable for Use in an Evaporative Light Scattering Detector An electronic circuit as shown in FIG. 9 was prepared and incorporated into an evaporative light scattering detector (ELSD) along with the drift tube of Example 1.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A composite tubular member comprising a tubular wall structure having a first end, a second end, an inner wall surface facing an interior of the tubular wall structure, and an outer wall surface, said tubular wall structure comprising an inner layer of a first metal and an outer layer of a second metal, said second metal having a higher coefficient of heat transfer compared to said first metal.

2. The composite tubular member of claim 1, wherein an outer surface of said inner layer is in contact with an inner surface of said outer layer.

3. The composite tubular member of claim 1, wherein the tubular wall structure comprises an outer sleeve of said second metal and an inner sleeve of said first metal, wherein an inner surface of said inner sleeve forms the inner wall surface.

4. The composite tubular member of claim 1, wherein the inner sleeve comprises flange portions on opposite ends of the inner sleeve, said flange portions forming the first end and second end of the tubular wall structure.

5. The composite tubular member of claim 1, wherein the outer wall surface of the tubular wall structure is a continuous surface that extends around a majority of an outer periphery of the tubular wall structure.

6. The composite tubular member of claim 1, wherein the first end of the tubular wall structure has an inlet cross-sectional flow area, the second end of the tubular wall structure has an outlet cross-sectional flow area, and the tubular wall structure has a tubular cross-sectional flow area between the first end and the second end, said tubular cross-sectional flow area being substantially equal to the inlet cross-sectional flow area, the outlet cross-sectional flow area, or both.

7. The composite tubular member of claim 6, wherein the tubular cross-sectional flow area is substantially equal to both the inlet cross-sectional flow area and the outlet cross-sectional flow area.

8. The composite tubular member of claim 7, wherein each of the tubular cross-sectional flow area, the inlet cross-sectional flow area, and the outlet cross-sectional flow area has a circular cross-sectional flow area.

9. The composite tubular member of claim 1, wherein the tubular wall structure has a wall thickness of at least about 2.54 mm (0.10 in).

10. The composite tubular member of claim 1, wherein the inner layer has a wall thickness of from about 2.54 mm (0.10 in) to about 5.08 mm (0.20 in), and the outer layer has a wall thickness of from about 2.54 mm (0.10 in) to about 7.62 mm (0.30 in).

11. The composite tubular member of claim 1, wherein said first metal comprises stainless steel, and said second metal comprises copper.

12. The composite tubular member of claim 1, further comprising one or more temperature sensors positioned along a length of said tubular wall structure.

13. The composite tubular member of claim 12, wherein said one or more temperature sensors are positioned along said outer wall surface of said tubular wall structure.

14. The composite tubular member of claim 12, wherein said one or more temperature sensors comprises at least two separate temperature sensors positioned along said tubular wall structure.

15. The composite tubular member of claim 14, wherein said tubular wall structure has a tubular midsection having a midsection length L, and wherein said at least two of said separate temperature sensors are positioned a distance of at least L/2 from one another along said tubular wall structure.

16. The composite tubular member of claim 1, further comprising a heating element positioned over said outer wall surface along a length of said tubular wall structure.

17. The composite tubular member of claim 16, wherein said heating element substantially covers all of said outer wall surface.

18. An evaporative light scattering detector comprising the composite tubular member of claim 1.

19. A method of analyzing a test sample that potentially contains at least one analyte, said method comprising the steps of:
    introducing the test sample into the composite tubular member of the evaporative light scattering detector of claim 18.

* * * * *